(12) United States Patent
Rajfer

(10) Patent No.: US 6,268,388 B1
(45) Date of Patent: Jul. 31, 2001

(54) METHOD FOR PREVENTING OR TREATING ERECTILE DYSFUNCTION BY ADMINISTERING AN ENDOTHELIN ANTAGONIST

(75) Inventor: Sol I. Rajfer, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/114,355

(22) Filed: Jul. 13, 1998

Related U.S. Application Data

(60) Provisional application No. 60/056,806, filed on Aug. 22, 1997.

(51) Int. Cl.$^7$ .................................................. A61K 31/42
(52) U.S. Cl. .......................................... 514/377; 514/380
(58) Field of Search ...................................... 514/377, 380

(56) References Cited

U.S. PATENT DOCUMENTS 5,612,359   3/1997   Murugesan ............................ 514/365
5,688,499   11/1997   Banting et al. .

FOREIGN PATENT DOCUMENTS

97/10821   3/1997   (WO) .
97/33608   9/1997   (WO) .

OTHER PUBLICATIONS

DeTejada, et al., "Endothelin: localization synthesis, activity, and receptor types in human penile corpus covernosum", Am. J. Physiol. 261 (Heart Circ. Physiol. 30): H1078–H1085, 1991.

Kifor et al., "Tissue Angiotensin II as a Modulator of Erectile Function. I. Angiotensin Peptide Content, Secretion and Effects in the Corpus Cavernosum", The Journal of Urology, vol. 157, pp. 1–6, Apr. 1997.

Medline abstract, AN 96408939, Boolell, M. et al., Apr. 1997.*

* cited by examiner

*Primary Examiner*—Russell Travers
(74) *Attorney, Agent, or Firm*—Ronald S. Hermenau

(57) ABSTRACT

Prevention or treatment of erectile dysfunction by administration of an endothelin antagonist.

4 Claims, No Drawings

METHOD FOR PREVENTING OR TREATING ERECTILE DYSFUNCTION BY ADMINISTERING AN ENDOTHELIN ANTAGONIST

This application claims priority from provisional U.S. application Ser. No. 60/056,806, filed Aug. 22, 1997, incorporated herein by reference in its entirety.

FIELD OF THE INVENTION

The present invention relates to the prevention or treatment of erectile dysfunction by administering an endothelin antagonist.

BRIEF DESCRIPTION OF THE INVENTION

Erectile dysfunction is the inability to obtain and maintain a penile erection sufficient for satisfactory intercourse or other sexual expression. A number of factors can place an individual at risk for this disorder, for example, trauma, pelvic surgery, hypercholesterolemia, ischemic heart disease, peripheral vascular disease, chronic renal failure, diabetes, or the use of medicaments such as antihypertensive medication or digoxin, or illicit drugs, cigarettes or alcohol. Methods for the treatment of erectile dysfunction include the use of vacuum devices and penile implants, as well as the administration of medicaments such as yohimbine, papaverine and apomorphine. Improved methods for the treatment of this disorder are sought, however, as the aforementioned methods do not provide sufficient efficacy, and/or are accompanied by drawbacks or side effects such as erosion, pain, priapism or gastrointestinal discomfort.

Endothelin peptides are potent constrictors of vascular and nonvascular smooth muscle and cause detumescence and vasoconstriction resulting in erectile dysfunction. Endothelin antagonists, which are compounds capable, inter alia, of inhibiting the binding of endothelin peptides to endothelin receptors, are useful in the treatment of endothelin-related disorders. The present invention provides a method for employing these compounds in the prevention or treatment of erectile dysfunction, as well as pharmaceutical compositions for this use.

DETAILED DESCRIPTION OF THE INVENTION

The present invention provides a method for the prevention or treatment of erectile dysfunction in a human, comprising administering to said human an endothelin antagonist in an amount effective therefor.

The endothelin antagonist employed may be any compound capable of inhibiting the action of endothelin peptides, especially, endothelin-1 (ET-1), endothelin-2 (ET-2) and/or endothelin-3 (ET-3). $ET_A$, $ET_B$ and $ET_{A/B}$ receptor antagonists may be employed. The endothelin antagonists described in the following documents, incorporated herein by reference in their entirety, are exemplary of those contemplated for use in the present method: U.S. Pat. No. 5,378,715; U.S. Pat. No. 5,514,696; U.S. Pat. No. 5,420,123; U.S. application Ser. No. 114,251, filed Aug. 30, 1993; U.S. application Ser. No. 08/728,238, filed Oct. 8, 1996; European Patent Application 702,012; U.S. Pat. No. 5,612,359; U.S. application Ser. No. 08/799,616, filed Feb. 13, 1997; U.S. application Ser. No. 08/692,869, filed Jul. 25, 1996; U.S. application Ser. No. 08/786,523, filed Jan. 21, 1997; U.S. application Ser. No. 08/810,777, filed Mar. 5, 1997; U.S. application Ser. No. 08/821,503, filed Mar. 21, 1997; World Patent Application 94/27979; U.S. Pat. No. 5,543,521; U.S. Pat. No. 5,464,853; U.S. Pat. No. 5,514,691; WO 96/06095; WO 95/08550; WO 95/26716; WO 96/11914; WO 95/26360; EP 601386; EP 633259; U.S. 5,292,740; EP 510526; EP 526708; WO 93/25580; WO 93/23404; WO 96/04905; WO 94/21259; GB 2276383; WO 95/03044; EP 617001; U.S. 5,334,598; WO 95/03295; GB 2275926; WO 95/08989; GB 2266890; EP 496452; WO 94/21590; WO 94/21259; GB 2277446; WO 95/13262; WO 96/12706; WO 94/24084; WO 94/25013; U.S. 5,571,821; WO 95/04534; WO 95/04530; WO 94/02474; WO 94/14434; WO 96/07653; WO 93/08799; WO 95/05376; WO 95/12611; DE 4341663; WO 95/15963; WO 95/15944; EP 658548; EP 555537; WO 95/05374; WO 95/05372; U.S. 5,389,620; EP 628569; JP 6256261; WO 94/03483; EP 552417; WO 93/21219; EP 436189; WO 96/11927; JP 6122625; JP 7330622; WO 96/23773; WO 96/33170; WO 96/15109; WO 96/33190; U.S. 5,541,186; WO 96/19459; WO 96/19455; EP 713875; WO 95/26360; WO 96/20177; JP 7133254; WO 96/08486; WO 96/09818; WO 96/08487; WO 96/04905; EP 733626; WO 96/22978; WO 96/08483; JP 8059635; JP 7316188; WO 95/33748; WO 96/30358; U.S. 5,559,105; WO 95/35107; JP 7258098; U.S. 5,482,960; EP 682016; GB 2295616; WO 95/26957; WO 95/33752; EP 743307; and WO 96/31492; such as the following compounds described in the recited documents: BQ-123 (Ihara, M., et al., "Biological Profiles of Highly Potent Novel Endothelin Antagonists Selective for the $ET_A$ Receptor", *Life Sciences*, Vol. 50(4), pp. 247–255 (1992)); PD 156707 (Reynolds, E., et al., "Pharmacological Characterization of PD 156707, an Orally Active $ET_A$ Receptor Antagonist", *The Journal of Pharmacology and Experimental Therapeutics*, Vol. 273(3), pp. 1410–1417 (1995)); L-754,142 (Williams, D. L., et al., "Pharmacology of L-754,142, a Highly Potent, Orally Active, Nonpeptidyl Endothelin Antagonist", *The Journal of Pharmacology and Experimental Therapeutics*, Vol. 275(3), pp. 1518–1526 (1995)); SB 209670 (Ohlstein, E. H., et al., "SB 209670, a rationally designed potent nonpeptide endothelin receptor antagonist", *Proc. Natl. Acad. Sci. USA*, Vol. 91, pp. 8052–8056 (1994)); SB 217242 (Ohlstein, E. H., et al., "Nonpeptide Endothelin Receptor Antagonists. VI:Pharmacological Characterization of SB 217242, A Potent and Highly Bioavailable Endothelin Receptor Antagonist", *The Journal of Pharmacology and Experimental Therapeutics*, Vol. 276(2), pp. 609–615 (1996)); A-127722 (Opgenorth, T. J., et al., "Pharmacological Characterization of A-127722: An Orally Active and Highly Potent $ET_A$ Selective Receptor Antagonist", *The Journal of Pharmacology and Experimental Therapeutics*, Vol. 276(2), pp.473–481 (1996)); TAK-044 (Masuda, Y., et al., "Receptor Binding and Antagonist Properties of a Novel Endothelin Receptor Antagonist, TAK-044 {Cyclo[D-α-Aspartyl-3[(4-Phenylpiperazin-1-yl) Carbonyl]-L-Alanyl-L-α-Aspartyl-D-2-(2 Thienyl)Glycyl-L-Leucyl-D-Tryptophyl]Disodium Salt}, in Human Endothelin$_A$ and Endothelin$_B$ Receptors", *The Journal of Pharmacology and Experimental Therapeutics*, Vol. 279(2), pp. 675–685 (1996)); bosentan (Ro 47-0203, Clozel, M., et al., "Pharmacological Characterization of Bosentan, A New Potent Orally Active Nonpeptide Endothelin Receptor Antagonist", *The Journal of Pharmacology and Experimental Therapeutics*, Vol. 270(1), pp. 228–235 (1994)); and TBC-11251, i.e.:

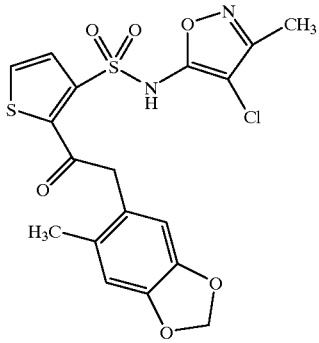

(IBC International Conference on Endothelin Inhibitors, Coronado, Calif. (Feb 1996) and 211 th American Chemical Society National Meeting, New Orleans, La. (March 1996)). These exemplary compounds may, for example, be prepared by methods, and employed at dosages, such as those described in the aforementioned documents.

Nonpeptide endothelin antagonists, especially sulfonamide endothelin antagonists (i.e., those containing a sulfonamide moiety —SO$_2$—NH—) are preferred, particularly those described in European Patent Application 702,012; U.S. Pat. No. 5,612,359; U.S. application Ser. No. 08/799, 616, filed Feb. 13, 1997; and U.S. application Ser. No. 60/035,832, filed Jan. 30, 1997. Especially preferred are the following compounds:

N-(3,4-dimethyl-5-isoxazolyl)-4'-(2-oxazolyl) [1,1'-biphenyl]-2-sulfonamide, having the structure:

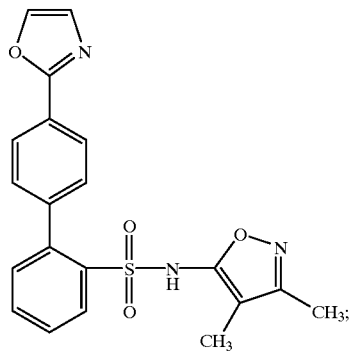

N-[[2'-[[(4,5-dimethyl-3-isoxazolyl)amino]sulfonyl]-4-(2 oxazolyl) [1,1'-biphenyl]-2-yl]methyl]-N,3,3-trimethylbutanamide, having the structure:

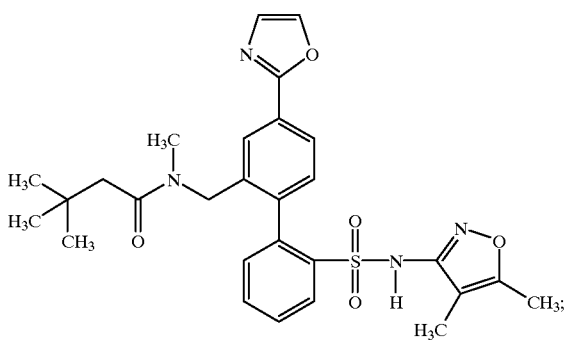

and pharmaceutically acceptable salts thereof.

The endothelin antagonist may be administered in any suitable manner such as orally, buccally, by injection or parenterally, in an effective amount, such as within a dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) in single or 2 to 4 divided daily doses.

The present invention also provides pharmaceutical compositions for the prevention or treatment of erectile dysfunction, comprising an endothelin antagonist in an amount effective therefor and a pharmaceutically acceptable vehicle or diluent. The endothelin antagonist can be utilized in a composition such as tablet, capsule, sterile solution or suspension, compounded in a conventional manner with a physiologically acceptable vehicle or carrier, excipient, binder, preservative, stabilizer, flavor, etc. as called for by accepted pharmaceutical practice.

In the methods and compositions of the present invention, the endothelin antagonist may, for example, be employed alone, in combination with one or more other endothelin antagonists, or with another compound useful for the prevention or treatment of erectile dysfunction, such as angiotensin converting enzyme (ACE) inhibitors such as captopril; dopamine receptor agonists such as apomorphine; renin inhibitors; angiotensin II (AII) antagonists such as irbesartan ((2 n-butyl-4-spirocyclopentane-1-[(2'-(tetrazol-5-yl) biphenyl-4-yl)methyl]-2-imidazolin-5-one); dual NEP-ACE inhibitors such as [4S-[4α(R*), 7α, 10aβ]]-octahydro-4-(2-mercapto-1-oxo-3-phenylpropyl)amino]-5-oxo-7H-pyrido [2,1-b][1,3]thiazepine-7-carboyxlic acid (BMS-186716, U.S. Pat. No. 5,508,272), [S-(R*,R*)]-hexahydro-6-[(2-mercapto-1-oxo-3-phenylpropyl)amino]-2,2-dimethyl-7-oxo-1H-azepine-1-acetic acid (BMS-189921, U.S. Pat. No. 5,552,397), alatriopril, sampatrilat, MDL 100240, and CGS 30440; PDE V inhibitors such as sildenafil (see Terrett et al., *Bioorg. Med. Chem. Ltrs.*, 6, 1819–1824 (1996)), GF 196960 and IC-351; alpha adrenergic blockers such as phentolamine; vasoactive intestinal peptide (VIP); and prostaglandin E$_1$ acting compounds such as alprostadil. Such other pharmaceutically active agents may be administered prior to, during or together with, or following administration of the endothelin antagonist. If formulated as a fixed dose, such combination products preferably employ the endothelin antagonists within the dosage range described above and the other pharmaceutically active agent within its approved dosage range.

What is claimed is:

1. A method for preventing or treating erectile dysfunction in a human, comprising administering to said human a biphenyl sulfonamide endothelin antagonist selected from N-[[2'-[[(4,5-dimethyl-3-isoxazolyl)amino]sulfonyl]-4-(2-oxazolyl)[1,1'-biphenyl]-2-yl]methyl]-N,3,3-trimethylbutanamide and N-(4,5-dimethyl-3-isoxazolyl)-2'-[(3,3-dimethyl-2-oxo-1-pyrrolidinyl)methyl]-4'-(2-oxazolyl)[1,1'-biphenyl]-2-sulfonamide, and salts thereof, in an amounteffective therefore.

2. A method for preventing or treating erectile dysfunction in a human, comprising administering to said human a biphenyl sulfonamide endothelin antagonist in an amount effective therefore.

3. The method of claim 1, wherein said biphenyl sulfonamide endothelin antagonist is administered in combination with one or more PDE V inhibitors.

4. The method of claim 3 wherein the PDE V inhibitors include sildenafil.

* * * * *